(12) United States Patent
Plotnikov

(10) Patent No.: US 7,389,206 B2
(45) Date of Patent: Jun. 17, 2008

(54) INSPECTION SYSTEMS AND METHODS OF OPERATION

(75) Inventor: Yuri Alexeyevich Plotnikov, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/502,199

(22) Filed: Aug. 10, 2006

(65) Prior Publication Data

US 2008/0040053 A1    Feb. 14, 2008

(51) Int. Cl.
  *G06F 15/00* (2006.01)
(52) U.S. Cl. .................................... 702/189
(58) Field of Classification Search ............ 702/189; 324/529, 307, 225
  See application file for complete search history.

(56) References Cited

U.S. PATENT DOCUMENTS

| | | |
|---|---|---|
| 3,875,502 A | 4/1975 | Neumaier |
| 4,031,004 A | 6/1977 | Sommer, Jr. et al. |
| 4,069,145 A | 1/1978 | Sommer, Jr. et al. |
| 4,188,577 A | 2/1980 | Mhatre et al. |
| 4,292,589 A | 9/1981 | Bonner |
| 4,481,821 A | 11/1984 | Chamuel |
| 4,495,466 A | 1/1985 | Lakin |
| 4,600,356 A | 7/1986 | Bridges et al. |
| 4,627,294 A | 12/1986 | Lew |
| 4,733,189 A | 3/1988 | Punchard et al. |
| 4,843,319 A | 6/1989 | Lara |
| 4,990,851 A | 2/1991 | Spies |
| 5,006,800 A | 4/1991 | Hedengren et al. |
| 5,056,049 A | 10/1991 | O'Neill |
| 5,262,722 A | 11/1993 | Hedengren et al. |
| 5,389,876 A | 2/1995 | Hedengren et al. |
| 5,391,988 A | 2/1995 | Kitagawa |
| 5,434,506 A | 7/1995 | Flora |
| 5,491,409 A | 2/1996 | Flora et al. |
| 5,659,248 A | 8/1997 | Hedengren et al. |
| 6,037,768 A * | 3/2000 | Moulder et al. ............ 324/225 |
| 6,124,712 A | 9/2000 | Chaiken |
| 6,135,627 A | 10/2000 | Beissner et al. |

(Continued)

FOREIGN PATENT DOCUMENTS

EP    0512796    11/1992

(Continued)

OTHER PUBLICATIONS

D. J. Brown, "Massively Multiplexed Eddy Current Testing and its Comparison With Pulsed Eddy Current Testing," Quantitative Nondestructive Evaluation, AIP Conference Proceedings, vol. 700, pp. 390-397, Feb. 2004.

(Continued)

*Primary Examiner*—John E. Barlow, Jr.
*Assistant Examiner*—Xiuquin Sun
(74) *Attorney, Agent, or Firm*—Penny A. Clarke; Patrick K. Patnode

(57) ABSTRACT

A method for inspecting an object is provided. The method includes applying a pulsed excitation signal to the object and detecting a transient response signal to the pulsed excitation signal. The method also includes convolving the transient response signal with a plurality of orthogonal functions to generate a plurality of orthogonal components.

19 Claims, 9 Drawing Sheets

U.S. PATENT DOCUMENTS

| | | | |
|---|---|---|---|
| 6,150,809 | A | 11/2000 | Tiernan et al. |
| 6,259,826 | B1 | 7/2001 | Pollard et al. |
| 6,285,183 | B1 | 9/2001 | Collingwood et al. |
| 6,344,741 | B1 | 2/2002 | Giguere et al. |
| 6,366,085 | B1 | 4/2002 | Yeshurun et al. |
| 6,424,151 | B2 | 7/2002 | Kawata et al. |
| 6,504,363 | B1 | 1/2003 | Dogaru et al. |
| 6,563,308 | B2 | 5/2003 | Nagano et al. |
| 6,573,721 | B1 | 6/2003 | Cull |
| 6,720,775 | B2 | 4/2004 | Plotnikov et al. |
| 6,911,826 | B2 * | 6/2005 | Plotnikov et al. ............ 324/529 |
| 6,949,922 | B2 | 9/2005 | Twerdochlib et al. |
| 6,952,095 | B1 | 10/2005 | Goldfine et al. |
| 6,961,113 | B1 | 11/2005 | Hayashi et al. |
| 6,972,561 | B2 | 12/2005 | Fields et al. |
| 6,989,679 | B2 | 1/2006 | Lieder et al. |
| 7,005,851 | B2 | 2/2006 | May et al. |
| 2005/0040821 | A1 * | 2/2005 | Hargreaves et al. ......... 324/307 |

FOREIGN PATENT DOCUMENTS

EP 0533440 3/1993

OTHER PUBLICATIONS

Y. A. Plotnikov et al., "Defect Characterization in Multi-Layered Conductive Components With Pulsed Eddy Current," D.O. Thompson and D.E. Chimenti (Eds.), Review of Progress in QNDE, vol. 21B, AIP, N.Y., 2002, pp. 1976-1983.

R. Rempt, "Scanning with Magnetoresistive Sensors for Subsurface Corrosion," D.O. Thompson & D.E. Chimenti (Eds.), Review of Progress in QNDE, vol. 21B, AIP, N.Y., 2002, pp. 1771-1778.

J. H. V. Lefebvre et al., "Pulsed Eddy Current Empirical Modeling," Proc. Vth International Workshop, Advances in Signal Processing for Non Destructive Evaluation of Materials, Quebec City, Canada Aug. 2-4, 2005, ISBN 2-9809199-0-X, pp. 69-74.

Robert A. Smith et al., "Rapid large-area transient eddy-current inspection using arrays," QinetiQ Ltd. UK, 2003.

Jim Cox et al., "Eddy Current Instrumentation," Oct. 2003, pp. 1-29.

C. M. Hils et al., "Flaw Imaging Using the Massively Multiplexed Eddy Current Technique," Oct. 2003, pp. 1-11.

Freda Sedgwick, "QinetiQ," (www.QinetiQ.com), Presentation to Earto technology Licensing Working, Feb. 15, 2002.

Y. Plotnikov et al., "Pulsed Eddy Current Pipeline Inspection System and Method," U.S. Appl. No. 11/290,916, filed Nov. 30, 2005.

Center Lines, "X-Probe: Eddy Current Array Probe as a High-Speed Alternative to Rotating Probes," Electric Power Research Institute, Inc., NDE Center, vol. 10, No. 11, pp. 1-8.

R. A. Smith et al., "Advances in Transient Eddy-current Imaging for Aerospace Applications," Published in Proc. World Conference on NDT, Montreal, 2004, Paper TS2.10.4, pp. 1-7.

Y. Danon et al., "Characterizing Tantalum Sputtered Coatings on Steel by Using Eddy Currents," IEEE Transactions on Magnetics, vol. 40, No. 54, Jul. 2004, pp. 1826-1832.

J. Skramstad et al., "Enhanced Detection of Deep Corrosion Using Transient Eddy Currents," Published in Proc. 7th Joint DoD/Faa/NASA Conference on Aging Aircraft, New Orleans, Sep. 2003, pp. 1-8.

H. L. Libby, "Introduction to Electromagnetic Nondestructive testing," Wiley—Interscience, 1971, Chapter 8.

* cited by examiner

INSPECTION SYSTEMS AND METHODS OF OPERATION

BACKGROUND

The invention relates generally to inspection systems and, more particularly, to pulsed eddy current inspection systems for defect detection in an object.

Corrosion and crack detection is desirable in metallic and other electro-conductive components and systems, such as an aircraft fuselage or oil pipeline, to ensure the structural integrity thereof. Nondestructive evaluation (NDE) techniques are being pursued to inspect such components and systems. Eddy current inspection techniques are often employed to inspect metallic airframe components. In order to inspect for corrosion at different depths, it is desirable that multi-frequency inspection be performed. Further, additional phase analysis of the eddy current response may be employed to increase signal-to-noise ratio and to improve defect detection, which leads to a powerful multi-frequency and phase analysis (MFPA) approach. However, conventional eddy current inspection systems with MFPA capability typically employ harmonic excitation techniques that use a series of excitations by varying the frequency of excitation each time to inspect different depths within the object. Accordingly, it is time consuming to gather inspection data using these techniques in addition, the excitation sources used with harmonic excitation techniques can be relatively expensive.

Pulsed eddy current (PEC) inspection is one possible solution, in that PEC systems inspect a component using multi-frequency nature of excitation pulses. Further, the time domain analysis techniques are applied to the PEC response. Several known PEC inspection systems characterize the PEC response curve using a single data point, such as the time to the maximum peak, the time to zero crossing of the curve or similar techniques. Furthermore, for inspecting relatively thicker objects a number of time windows are employed for obtaining data points corresponding to different layers of the object. Unfortunately, this technique has an undesirable low signal to noise ratio for signals corresponding to deeper defects in the objects. Certain other PEC inspection systems employ filters and time average of the transient signal to provide a better noise resistance. However, these systems are typically tuned to a particular application and are not as comprehensive as the EC method with harmonic excitation. In addition, such systems lack commonality with the conventional EC method with harmonic excitation analysis, which is adopted by the NDE community and widely used by inspectors and automated inspection systems for a variety of industrial applications.

Accordingly, it would be desirable to develop an inspection system that provides the MFPA capability of harmonic excitation techniques with faster inspection times and relatively lower cost excitation sources.

BRIEF DESCRIPTION

Briefly, according to one embodiment of the invention, a method for inspecting an object is provided. The method includes applying a pulsed excitation signal to the object and detecting a transient response signal to the pulsed excitation signal. The method also includes convolving the transient response signal with a plurality of orthogonal functions to generate a plurality of orthogonal components.

In another embodiment, a method for inspecting an object is provided. The method includes applying a pulsed excitation signal to the object, detecting a transient response signal to the pulsed excitation signal and convolving the transient response signal with a plurality of functions to generate a plurality of orthogonal components. The functions are selected from the group consisting of a triangular wave, a rectangular wave, a trapezoidal wave and combinations thereof.

In another embodiment, an inspection system is provided. The inspection system includes a pulse generator configured to supply a pulsed excitation signal and a probe configured to receive the pulsed excitation signal, to transmit electromagnetic flux into an object under test, and to sense and generate output signals from transient electromagnetic flux in the object. The inspection system also includes an analog-to-digital converter configured to digitize the output signals from the probe and to supply a digitized transient response signal and a processor configured to convolve the digitized transient response signal with a plurality of orthogonal functions to generate a plurality of orthogonal components.

In another embodiment, an inspection system is provided. The inspection system includes a pulse generator configured to supply a pulsed excitation signal and a probe configured to receive the pulsed excitation signal, to transmit electromagnetic flux into an object under test, and to sense and generate output signals from transient electromagnetic flux in the object. The inspection system also includes at least one integrator configured to receive the output signals from the probe and to convolve the output signals with a plurality of functions to generate a plurality of orthogonal components. The functions are selected from the group consisting of a triangular wave, a rectangular wave, a trapezoidal wave and combinations thereof.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
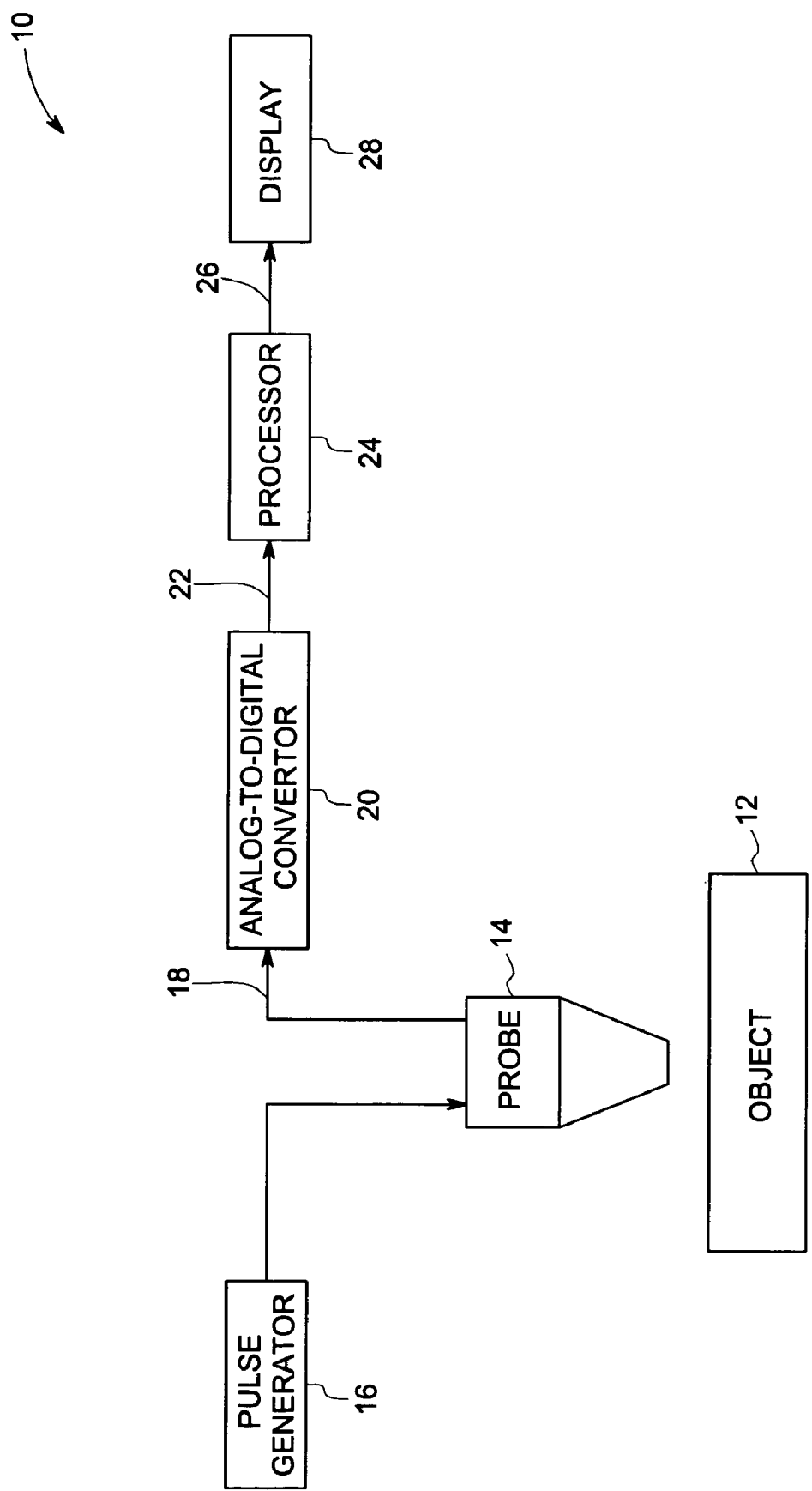
FIG. 1 is a diagrammatical representation of a pulsed eddy current inspection system, in accordance with an exemplary embodiment of the present invention.

As discussed in detail below, embodiments of the present invention function to provide an inspection system that provides multi-frequency and phase analysis (MFPA) capability with relatively fast inspection times. In particular, the present invention facilitates generation of images corresponding to many frequencies from a single scan of an object thereby enabling defect detection in multiple layers of the object. Referring now to the drawings, FIG. 1 illustrates a pulsed eddy current inspection system 10 for inspecting an object 12 through a probe 14. The inspection system 10 includes a pulse generator 16 that is configured to supply a pulsed excitation signal to the probe 14. Further, the probe 14 is configured to transmit electromagnetic flux into the object 12 and to sense and generate an output signal 18 from transient electromagnetic flux in the object 12. The pulsed excitation introduces a wide range of frequencies (f) into the object 12 under test. In addition, the inspection system 10 includes an analog-to-digital converter 20 that is configured to digitize the output signal 18 from the probe 14 and to supply a digitized transient response signal such as represented by reference numeral 22 to a processor 24.

It should be noted that the present invention is not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

The processor 24 is configured to convolve the digitized transient response signal 22 with a number of orthogonal functions to generate a number of orthogonal components that will be described in a greater detail below. In one embodiment, the orthogonal functions include sine and cosine functions. In certain embodiments, the probe 14 may be attached to a two-dimensional mechanical raster scanner (not shown) to obtain transient responses from different positions over the object 14 as controlled by the scanner. In this exemplary embodiment, the processor 24 is configured to generate a number of linear profiles that correspond to the probe positions controlled by the mechanical scanner using the orthogonal components. Moreover, a two-dimensional plot of the linear profiles may be made available to a user via a display 28 coupled to the processor 24. As will be appreciated by one skilled in the art the processor 24 may include computational algorithms with embedded digital or analog signal processing for convolving the digitized transient response signals 22 and generating the linear profiles from the orthogonal components.

Figure 2:
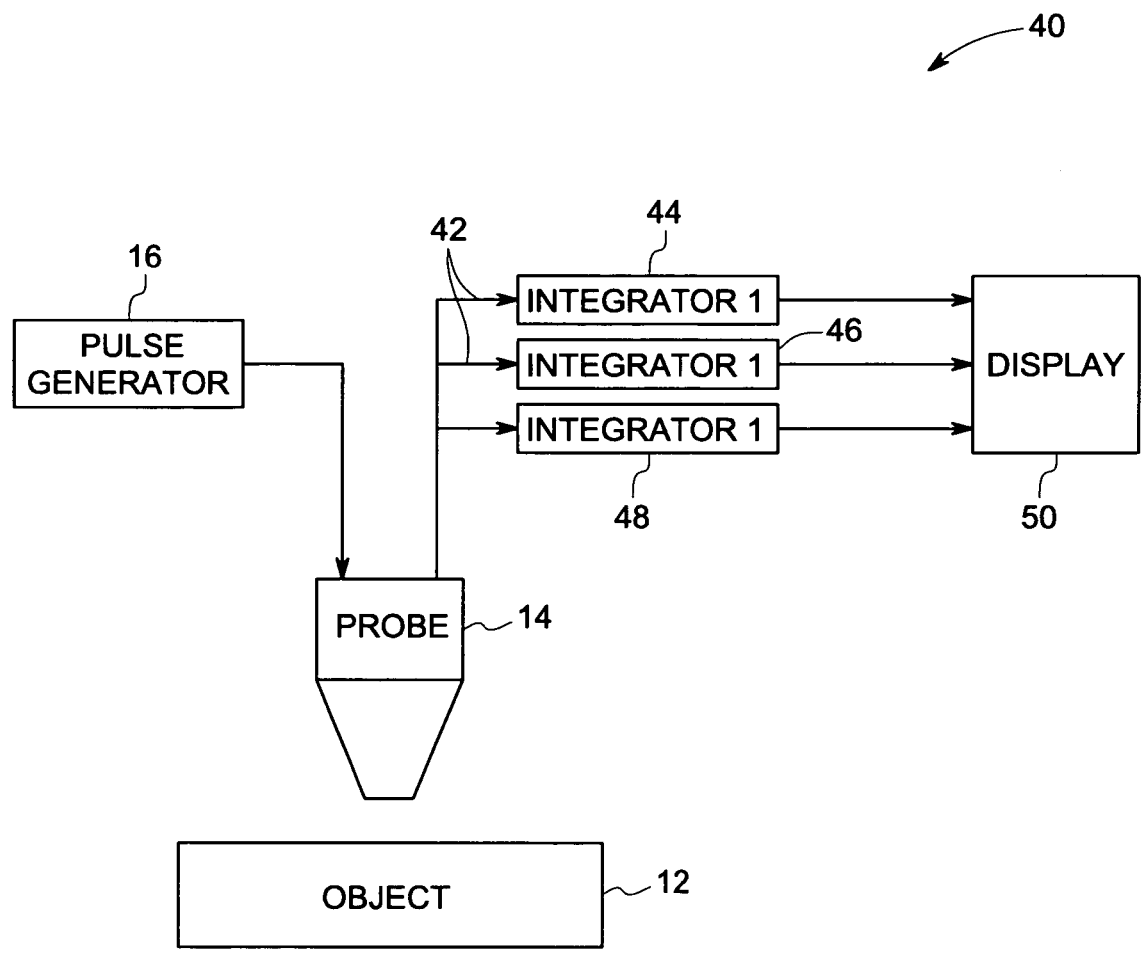
FIG. 2 is a diagrammatical representation of another pulsed eddy current inspection system embodiment of the present invention.

FIG. 2 is a diagrammatical representation of another pulsed eddy current inspection system embodiment 40 of the present invention. In operation, the probe 14 receives the pulsed excitation signal from the pulse generator 16 and generates an output signal 42 from transient electromagnetic flux in the object 12. In the illustrated embodiment, the inspection system 40 includes a number of integrators such as represented by reference numerals 44, 46 and 48 that are configured to receive the output signal 42 from the probe 14 and to convolve the output signal 42 with a number of functions to generate a plurality of orthogonal components. Further, in certain embodiments, the integrators 44, 46 and 48 are configured to convolve the output signal 42 at a number of frequencies to generate a plurality of orthogonal components that are corresponding to a respective depth in the object 12. Non-limiting examples of such functions include a sinusoidal wave, triangular wave, rectangular wave, trapezoidal wave and so forth. In the illustrated embodiment, the inspection system 40 includes three integrators. However, a greater or lesser number of integrators may be envisaged. As with the embodiment, of FIG. 1, the inspection system 40 also includes a display 50 configured to display a XY scatter plot of the linear profile in a complex plane that is generated from the orthogonal components. Beneficially, the embodiment described here with reference to FIG. 2 may be implemented into the front-end electronics with embedded digital or analog processing. Consequently, the illustrated embodiment facilitates the implementation of MFPA without requiring the use of a high-speed digitizer or the necessary computer power to perform the mathematical computations associated with more complex analytical functions, such as sine and cosine functions. This hardware implementation via integrated circuit electronics significantly improves the signal processing speed of the MFPA calculations.

Figure 3:
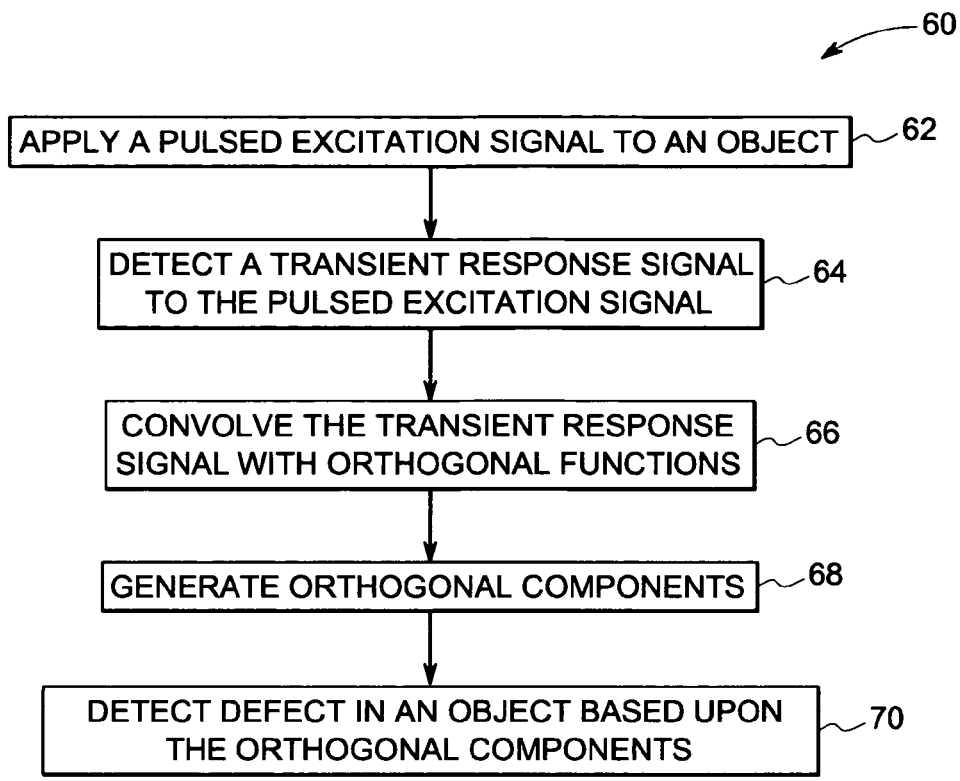
FIG. 3 is a flow chart illustrating a method for inspecting an object using the inspection systems of FIG. 1 or 2.

FIG. 3 is a flow chart illustrating a method 60 for inspecting an object using the inspection systems of FIG. 1 or 2. As illustrated, a pulsed excitation signal is applied to an object (step 62). At step 64, a transient response signal corresponding to the pulsed excitation signal is detected. The transient response signal is convolved with orthogonal functions (step 66) to generate orthogonal components, as represented by step 68. In one exemplary embodiment, the orthogonal functions include a sine function and a cosine function. In a more particular embodiment, the sine function takes the form of a discrete sine transform and the cosine function is a discrete cosine transform. These examples are illustrative and non-limiting. More generally, the orthogonal (also called unitary, if complex) functions may be any function $\phi_i$ defined in $a \leq x \leq b$ that satisfies the general condition:

$$\int_a^b \phi_i(x) \phi_j^*(x) dx = K_i \delta_{ij}$$

where $\delta_{ij}=1$ for i=j, and =0 for i≠j, and * is the complex conjugate.

The orthogonal components generated from the transient response signal are representative of a presence or an absence of a defect in the object. Moreover, in certain embodiments, a number of linear profiles are generated using the orthogonal components that are graphed in a complex plane to generate a XY scatter plot (complex plane trajectories or Lissajous). In one embodiment, the complex plane is an impedance plane. In particular, the discrete transforms are utilized to map real and imaginary components of the vector locus on the impedance plane for a selected frequency. In one embodiment, a phase shift ($\phi$) is determined for the transient response based upon a difference between an initial time ($T_0$) and a zero position of the sine function. Further, the linear profile or XY scatter plot may be adjusted using the phase shift ($\phi$). At step 70, defect detection is performed based upon the orthogonal components. The generation of orthogonal components from the transient response signal and defect detection based upon such components will be described below with reference to FIGS. 4-8.

Figure 4:
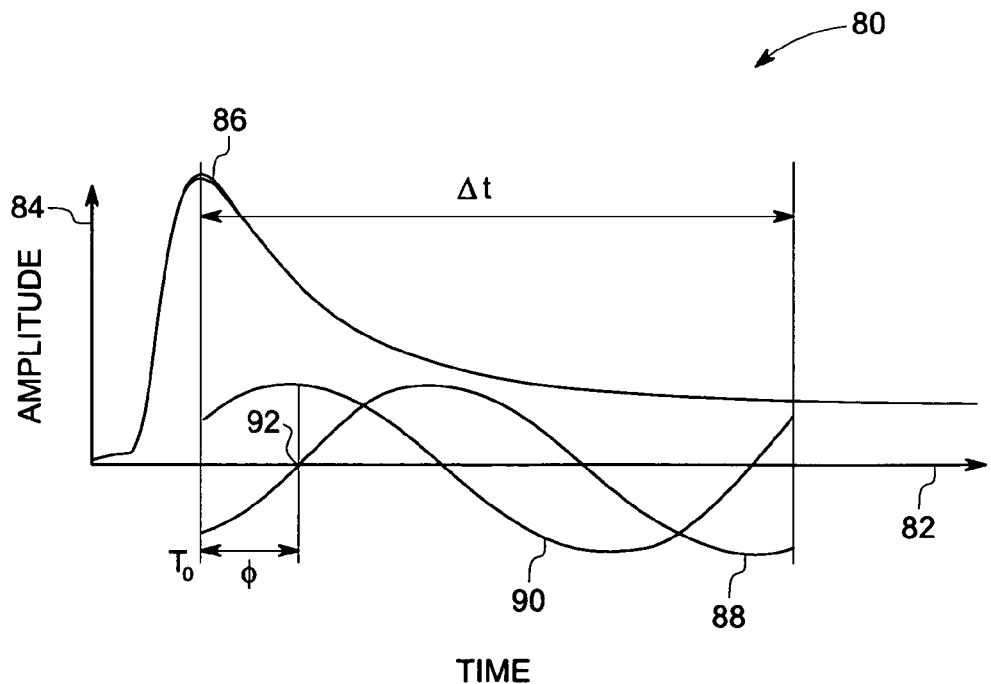
FIG. 4 is a graphical representation of a transient response signal obtained using the inspection system of FIG. 1 and exemplary orthogonal functions.

FIG. 4 is a graphical representation 80 of a transient response signal obtained using the inspection system 10 of FIG. 1. In the illustrated embodiment, the abscissa axis represents elapsed time (t) and the ordinate axis represents amplitude. The transient response signal received from the object 12 (see FIG. 1) in response to the applied pulsed excitation signal is indicated by reference numeral 86. In this exemplary embodiment, the transient response signal 86 is convolved with a sine function and a cosine function that are represented by reference numerals 88 and 90. For the embodiment illustrated in FIG. 1, the transient response signal 86 is digitized prior to convolving the transient response signal 86 with the orthogonal functions 88, 90. As will be appreciated by one skilled in the art, a variety of orthogonal functions may be employed to convolve the transient response signal for generating the orthogonal components for defect detection.

In this exemplary embodiment, a processing time ($\Delta t$) for the convolving step and a phase shift ($\phi$) are indicated in FIG. 4. It should be noted that the processing time ($\Delta t$) may be selected for the convolving step and defines a fundamental frequency (f=1/t) of the orthogonal component. In certain embodiments, the processing time ($\Delta t$) may be selected using conventional look-up tables for frequency for harmonic excitation techniques. In addition, the phase shift $\phi$ for the transient response signal 86 may be determined based upon an initial time ($T_0$) and a zero position 92 of the sine function 88. Such phase shift $\phi$ may be further employed to adjust a two-dimensional plot or linear profiles generated using the orthogonal functions.

Figure 5:
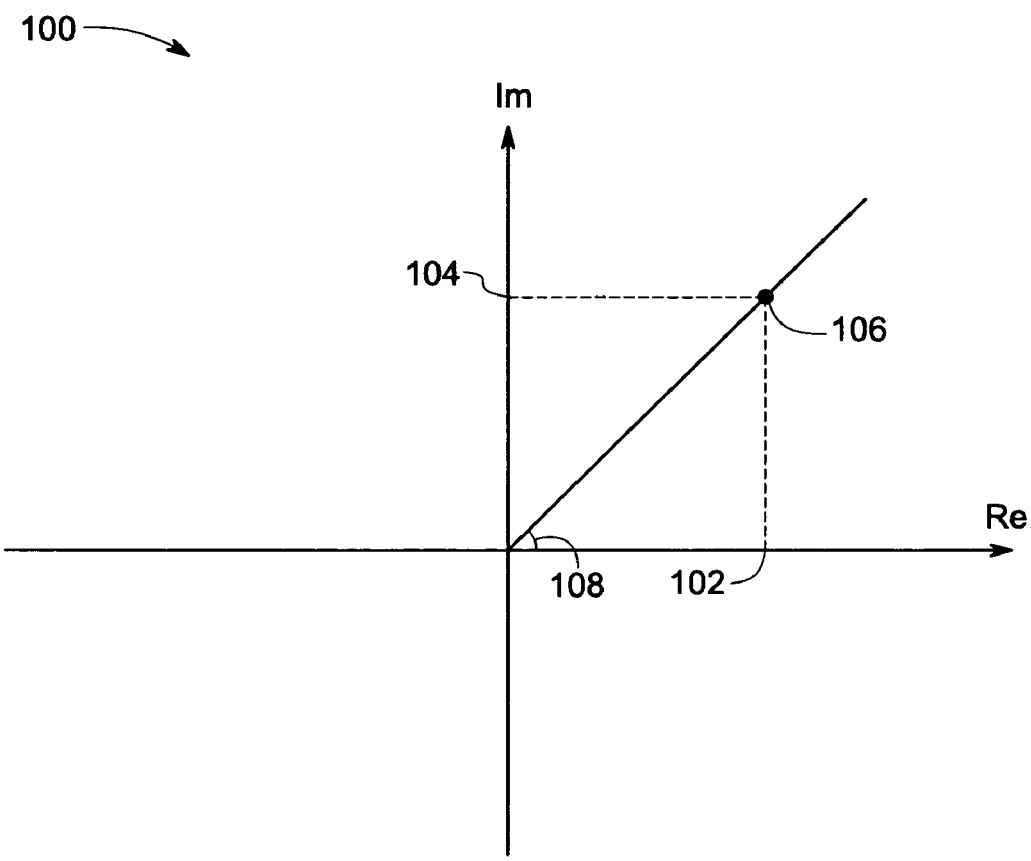
FIG. 5 is a graphical representation on a complex plane of a processed signal obtained by performing a discrete transform of the transient response signal of FIG. 4.

FIG. 5 is a graphical representation of a processed signal of orthogonal components 100 obtained by performing a discrete transform of the transient response signal 86 of FIG. 4. As described above, the transient response signal 86 is convolved with the discrete sine and cosine transforms to generate orthogonal components, in the illustrated embodiment. In this exemplary embodiment, the orthogonal components of the processed signal 106 include a real component ($S_{Re}$) 102 and an imaginary component ($S_{Im}$) 104. The real and imaginary components 102 and 104 are represented by the following equations:

$$S_{Re} = \frac{1}{N_2 - N_1} \sum_{n=N_1}^{N_2} U(n)\cos\left(\frac{2\pi(n - N_1)}{N_2 - N_1} + \phi\right) \quad (1)$$

$$S_{Im} = \frac{1}{N_2 - N_1} \sum_{n=N_1}^{N_2} U(n)\sin\left(\frac{2\pi(n - N_1)}{N_2 - N_1} + \phi\right) \quad (2)$$

where n is the number of time intervals for convolving the transient response signal 86, $N_1$ and $N_2$ are first and second time intervals and $\phi$ is a phase shift for the transient response signal 86.

Further, impedance plane trajectories (i.e., Lissajous) generated from such orthogonal components are graphed on the complex plane to represent a XY scatter plot of the orthogonal components 100. Alternately, the processed signal 106 can be characterized on the complex plane by phase 108 (angular measure) and magnitude (radial measure). It should be noted that the processed signal of the orthogonal components 100 represents the signal obtained by convolving the transient response signal 86 at a first frequency (f1=1/T1). In certain embodiments, the convolving step may be repeated for a number of frequencies represented by:

$$f_2 = \frac{1}{T_2}, \ldots, f_n = \frac{1}{T_n} \quad (3)$$

to generate sets of orthogonal components, where each of the sets of orthogonal components corresponds to a respective depth ($\Delta z$) in the object. The generation of the sets of orthogonal components for defect detection of a multi-layered object will be described below with reference to FIGS. 9 and 10.

Figure 6:
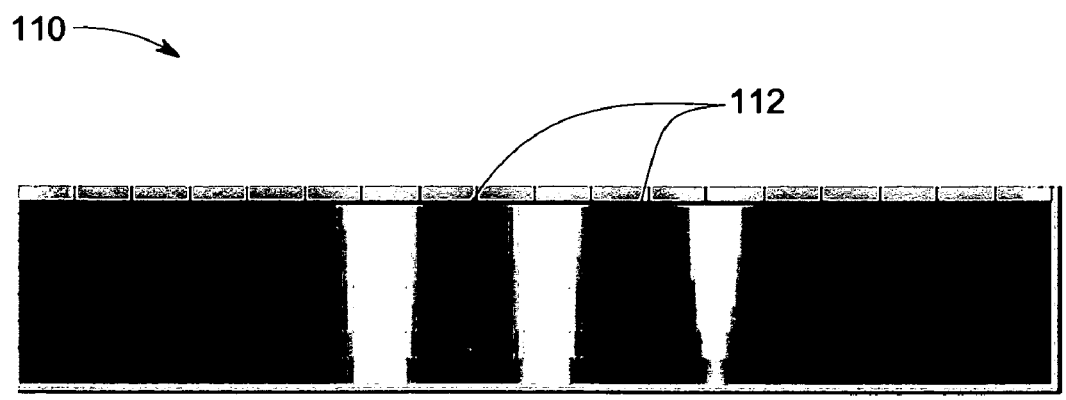
FIG. 6 is a two-dimensional scan image of an object for a single frequency obtained using the inspection system of FIG. 1.

FIG. 6 is a two-dimensional scan image 110 of an object for a single frequency obtained using the inspection system 10 of FIG. 1. In the illustrated embodiment, the image 110 is obtained using a two-dimensional mechanical scanner (not shown). The object 12 used for this scan is a multi-layer stack of aluminum plates with several artificial flaws located in different layers as illustrated below in FIG. 9. In the illustrated embodiment, the two-dimensional scan image 110 is a representation of magnitude of an orthogonal component computed from the transient response signal obtained from the probe 14 (see FIG. 1) for a single frequency. The defect-free areas in the object are represented by reference numerals 112. As described before, the transient response signal 86 (see FIG. 4) is convolved with orthogonal functions to generate orthogonal components. In the illustrated embodiment, the signal 86 is convolved with sine and cosine functions to generate the orthogonal components. The two-dimensional image 110 is the result of such convolution with a sine function for each position of the probe in the two-dimensional scan. Further, linear profiles are generated from the two-dimensional scan using such orthogonal components as illustrated in FIG. 7.

Figure 7:
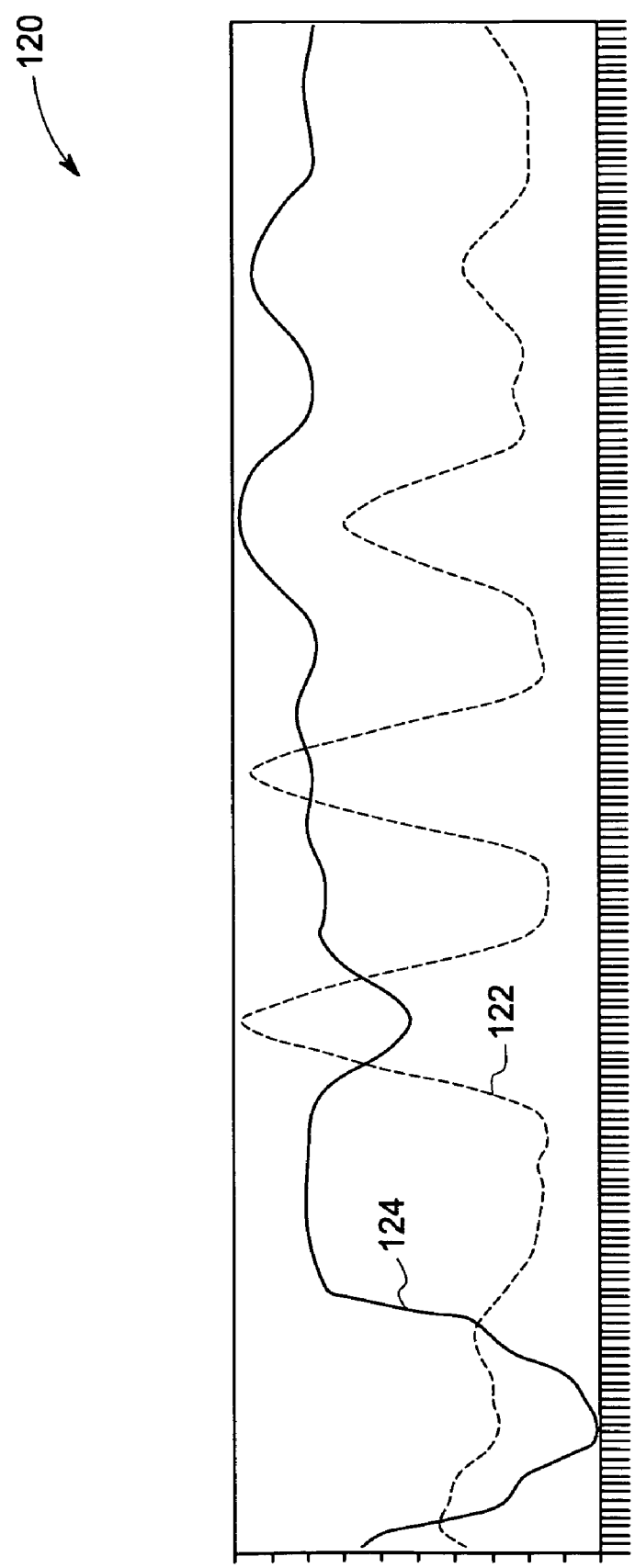
FIG. 7 is a graphical representation of linear profiles obtained by convolving a transient response signal with sine and cosine functions computed for a single horizontal line from the two-dimensional scan of FIG. 6.
Figure 8:
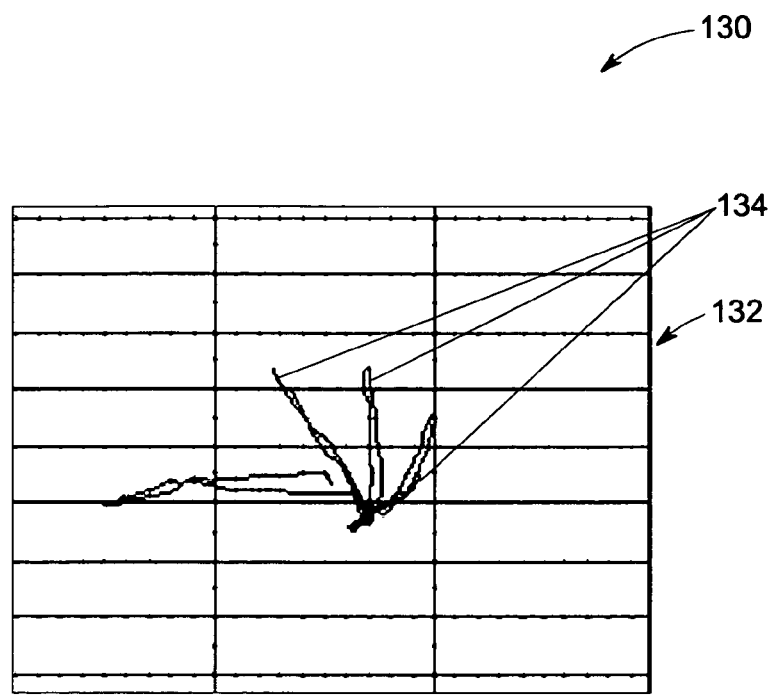
FIG. 8 is a graphical representation of linear profiles of FIG. 7 in a complex plane.

FIG. 7 is a graphical representation of linear profiles 120 of an object obtained by convolving a transient response signal obtained for each position in a horizontal line across the center of the two-dimensional scan 110 with sine and cosine functions. In the illustrated embodiment, the abscissa axis represents position of the probe and the ordinate axis represents amplitude of the orthogonal components. Further, linear profiles showing defects in different layers of the object computed with the sine and cosine transforms are represented by reference numerals 122 and 124 respectively. Moreover, such linear profiles 122 and 124 are graphed on a complex plane as illustrated in FIG. 8. FIG. 8 is a graphical representation 130 of linear profiles of FIG. 7 in a complex plane 132. In this embodiment, each pair of orthogonal components 122 and 124 from the linear profiles 120 of FIG. 7 is represented by horizontal (124) and vertical (122) coordinates of the complex plane 132. In this embodiment, the defects in different layers of the object are represented by reference numeral 134 on the complex plane 132. In particular, the defects located in different layers are shown on the complex plane 132 with different magnitudes and phase. In certain embodiments, the phase value of the defect indications 134 can be used as representative of a presence or absence of a defect or as representative of the depth of the defect in the inspected object. Further, a multi frequency analysis may be performed by changing a time interval for the convolution of the transient response signal 86 (see FIG. 4). In this embodiment, the time interval for the convolution and a phase shift may be adjusted to detect flaws in multiple layers of the object through the representation of the linear profiles on the complex plane 132. For example, a relatively long processing time may be selected for detection of deeper located defects in the object. The detection of defects for a multi-layered object through the multi frequency analysis will be described below with reference to FIGS. 9 and 10.

Figure 9:
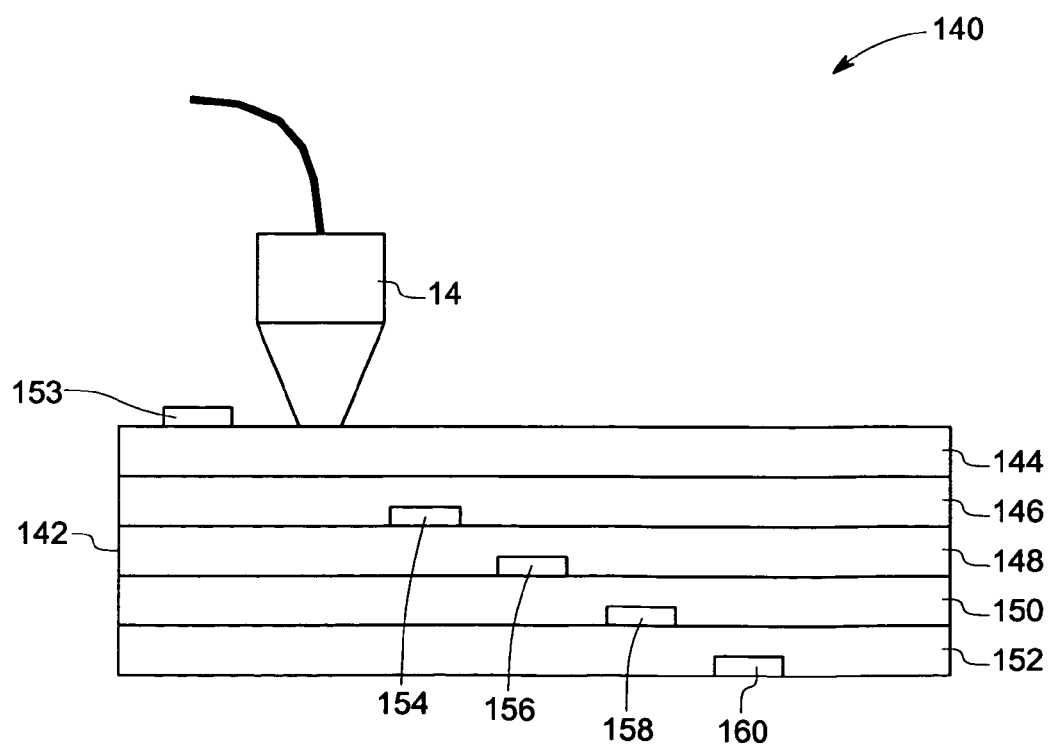
FIG. 9 is a diagrammatical representation of a pulsed eddy current inspection probe and a multi-layered object.

FIG. 9 is a diagrammatical representation 140 of the pulsed eddy current inspection probe 14 and a multi-layered object 142. As illustrated, the object 142 includes a number of layers such as represented by reference numerals 144, 146, 148, 150 and 152. The layers 144, 146, 148, 150 and 152 may include defects such as represented by reference numerals 154, 156, 158 and 160. In operation, a multi-frequency analysis may be performed by changing the time interval for convolution to detect the presence or absence of defects 154, 156, 158 and 160 in the layers 144, 146, 148, 150 and 152 or presence of the liftoff 153. As previously described, amplitude and phase analysis may be employed to detect and visualize the flaws such as 154, 156, 158 and 160 after converting the transient response from the probe 14 into the complex plane representation. In operation, the processing time interval and phase shift parameters may be adjusted to visualize flaws in a particular layer. In certain embodiments, a set of calibration specimens may be utilized to maximize signal from a defect located in a particular layer. Further, in certain embodiments, a set of processing parameters may be employed to generate simultaneous images of several layers for real-time processing of such images from a single scan.

Figure 10:
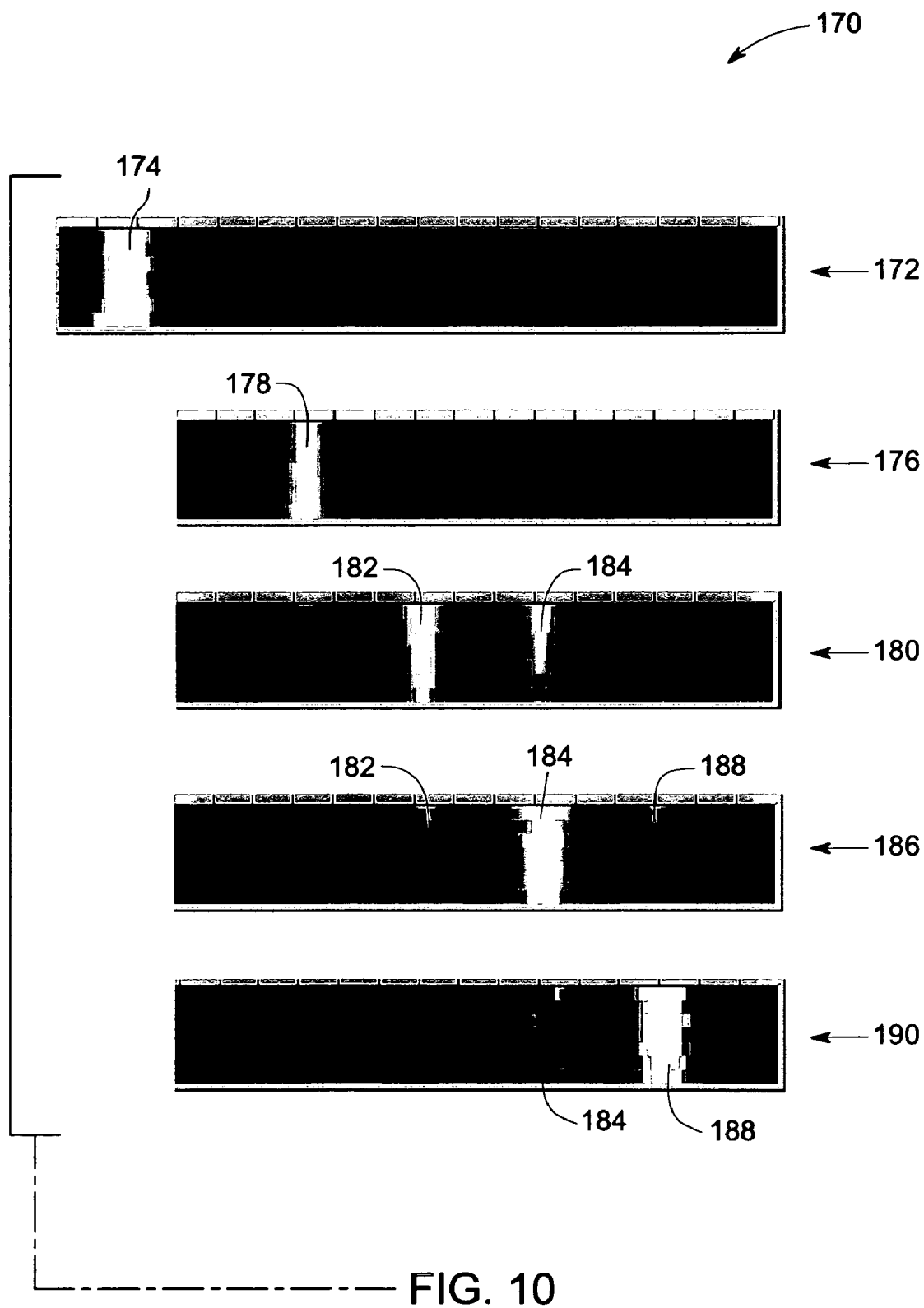
FIG. 10 shows images corresponding to different layers of the multi-layered object of FIG. 9.

FIG. 10 shows images 170 corresponding to different layers of the multi-layered object 142 of FIG. 9. As illustrated, a two-dimensional scan image 172 includes an indication 174 of the liftoff reference corresponding to the first layer 144 obtained by the probe 14. In this exemplary embodiment, multi-frequency analysis is employed to detect the defects in the subsequent layers 146, 148, 150 and 152. For example, an image 176 corresponding to the layer 146 includes indication 178 of the defect 154 in the layer 146. Similarly, an image 180 corresponding to the layer 148 includes indication 182 of the defect 156 in the layer 148. In addition, the image 180 may also include an indication 184 of a defect in deeper layers such as corresponding to the defect 158 in the layer 150. Further, as illustrated, an image 186 corresponding to the layer 150 includes the indication 184 corresponding to the defect 158 and 182 corresponding to the defect 156 in the layer 148. In addition, the image 186 also includes indication 188 corresponding to the defect 160 in the layer 152. Similarly, an image 190 corresponding to the layer 152 includes the response 188 corresponding to the defect 160 along with indication 184 corresponding to the defect 158. Thus, indications corresponding to shallow defects may be present in the lower frequency images. In certain embodiments, a linear combination of two or more images may be utilized to attenuate some indications from the shallow defects in the images of the deeper defects.

In the illustrated embodiment, the transient response signal from the different locations over the object 142 is convolved with a plurality of orthogonal functions to generate a plurality of orthogonal components as described above to form the images 172, 176, 180, 186 and 190 corresponding to different layers 144, 146, 148, 150 and 152. The convolving step is performed at a first frequency and is repeated for a plurality of frequencies to generate a plurality of sets of orthogonal components corresponding to a respective depth in the object 142. As described before, such orthogonal components are representative of the presence or an absence of the defects in the various layers. The orthogonal components real component (x component) and imaginary component (y component) can be converted to phase and amplitude and so forth. In this exemplary embodiment, the orthogonal functions include a sine function and a cosine function. However, other simplified functions may be employed for convolving the transient response signal to generate the orthogonal components, as discussed above with respect to the embedded electronics embodiment depicted in FIG. 2, for example. FIGS. 11-14 illustrate exemplary functions that may be employed for convolving the transient response signal obtained from the probe 14.

Figure 11:
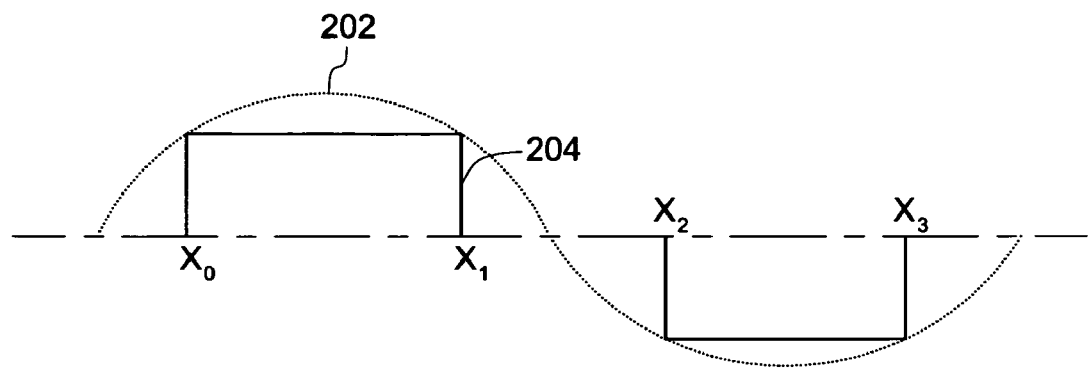
FIG. 11 is a graphical representation of an exemplary function employed for convolving the transient response signal of FIG. 4.
Figure 12:
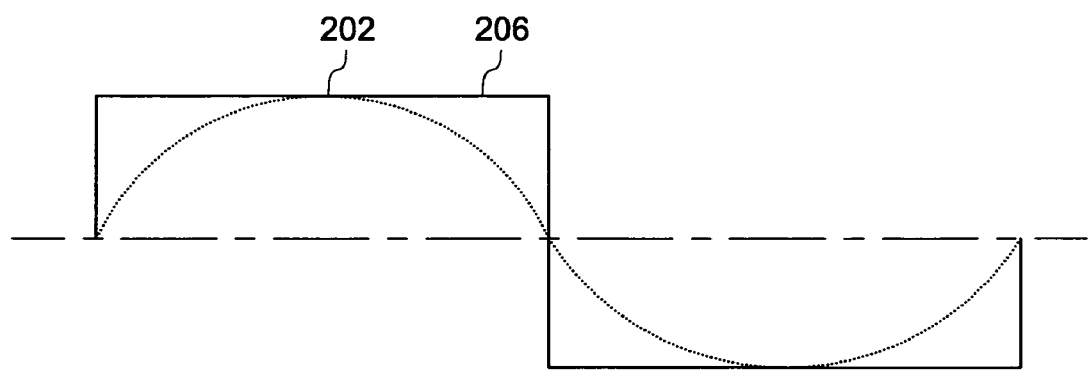
FIG. 12 is a graphical representation of another exemplary function employed for convolving the transient response signal of FIG. 4.
Figure 13:
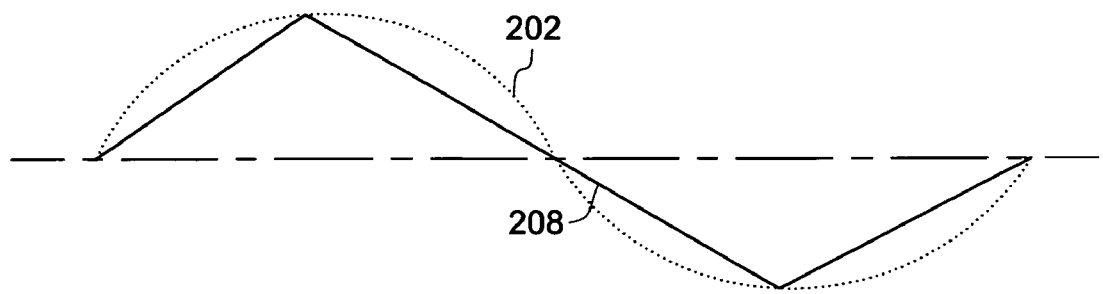
FIG. 13 is a graphical representation of another exemplary function employed for convolving the transient response signal of FIG. 4.
Figure 14:
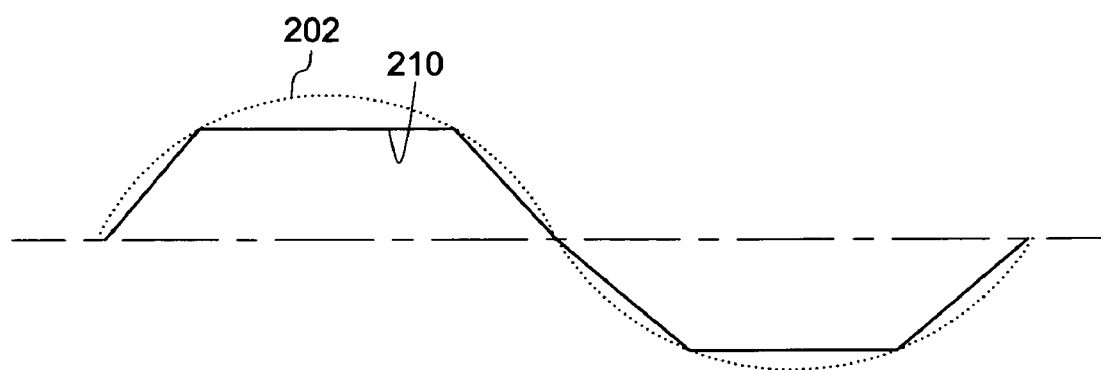
FIG. 14 is a graphical representation of another exemplary function employed for convolving the transient response signal of FIG. 4.

As illustrated in FIGS. 11 and 12, rectangular functions such as represented by reference numerals 204 and 206 may be used to approximate a sine or a cosine function 202 for convolving a transient response signal. Similarly, as illustrated in FIGS. 13 and 14 a triangular function 208 or a trapezoidal function 210 may be used to approximate the sine or the cosine function 202 for convolving the transient response signal. As will be appreciated by one skilled in the art a number of other functions may be used to convolve the transient response signal to generate the orthogonal components that are representative of the defects in an object. The relatively simple functions shown in FIGS. 11-14 are employed, for example, with the embedded electronics embodiment described above with reference to FIG. 2.

The various aspects of the methods and systems described hereinabove have utility in different NDT applications, such as in aerospace and oil and gas industries. The methods and systems described above allow defect detection in components through a multi-frequency and phase analysis (MFPA) utilizing transient eddy current response from an eddy current sensor. In particular, the methods and systems utilize a single two-dimensional scan to generate images for several frequencies that allows for defect detection in various layers of an object. Advantageously, these methods and systems provide faster inspection times and relatively lower cost excitation sources while providing relatively high signal to noise ratio for signals corresponding to deeper defects in the objects. Further, the method of processing of the transient response and further imaging the orthogonal components in the complex plane as described above provides a powerful tool that is already used by current EC systems with harmonic excitation. The operators of the existing EC systems are trained to work with complex plane trajectories (Lissajous) representations of various defects and interpretations of the Lissajous are included into the user manuals. Beneficially, the described above processing of the PEC response uses advantage of the previously developed and widely adopted EC imaging convention.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for inspecting an object, the method comprising:
   applying a pulsed excitation signal to the object;
   detecting a transient response signal to the pulsed excitation signal;
   selecting a segment of the transient response signal obtained over a time interval $\Delta t$;
   convolving the transient response signal obtained over the time interval $\Delta t$ with a plurality of orthogonal functions to generate a plurality of orthogonal components corresponding to a fundamental frequency $f=1/\Delta t$, wherein the convolving step is performed at a first frequency $f1=1/\Delta t$;
   using the plurality of orthogonal components corresponding to the fundamental frequency $f=1/\Delta t$ to detect a presence or an absence of a defect in the object; and
   selecting a plurality of segments of the transient response signal obtained over respective time intervals $\{\Delta t2, \ldots \Delta tn\}$, wherein the convolving step is repeated for the plurality of segments to generate a plurality of sets of orthogonal components corresponding to respective ones of a plurality of frequencies $f=\{1/\Delta t2, \ldots, 1/\Delta tn\}$, and wherein each of the sets of orthogonal components corresponds to a respective depth $\Delta z$ in the object.

2. The method of claim 1, further comprising generating a plurality of linear profiles using the orthogonal components.

3. The method of claim 2, further comprising graphing the linear profiles in a complex plane.

4. The method of claim 1, further comprising digitizing the transient response signal prior to convolving the transient response signal.

5. The method of claim 1, wherein the orthogonal functions comprise a sine function and a cosine function.

6. The method of claim 5, further comprising:
   generating a plurality of linear profiles using the orthogonal components;
   graphing the linear profiles in a complex plane to generate a XY scatter plot;
   determining a phase shift ($\phi$) for the transient response signal based on a difference between an initial time ($T_o$) and a zero position of the sine function; and
   adjusting the XY scatter plot using the phase shift ($\phi$).

7. The method of claim 1, wherein the sine function comprises a discrete sine transform $$\sin\left(\frac{2\pi(n-N_1)}{N_2-N_1}+\phi\right)$$

and the cosine function comprises a discrete cosine transform $$\cos\left(\frac{2\pi(n-N_1)}{N_2-N_1}+\phi\right),$$

wherein n is the number of time intervals for convolving the transient response signal, $N_1$ and $N_2$ are first and second time intervals and $\phi$ is a phase shift for the transient response signal.

8. The method of claim 1, wherein the object comprises a plurality of layers, and wherein each of the sets of orthogonal components corresponds to a respective one of the layers.

9. The method of claim 1, further comprising forming a linear combination of a plurality of the orthogonal components for different ones of the frequencies $\{f1, \ldots, fn\}$.

10. The method of claim 1, wherein the orthogonal components are selected from the group consisting of a real component, an imaginary component, a phase, an amplitude and combinations thereof.

11. The method of claim 1, wherein the orthogonal components define a graphical position of the processed transient response on a XY scatter plot and phase, or magnitude are representative of a presence or absence of a defect, or are representative of a depth of the defect in the object.

12. The method of claim 1, further comprising:
    digitizing the transient response signal prior to convolving the transient response signal; and
    selecting a processing time for the convolving step, wherein the processing time T defines a fundamental frequency $f=1/T$ of the orthogonal component.

13. An inspection system, comprising:
    a pulse generator configured to supply a pulsed excitation signal;
    a probe configured to receive the pulsed excitation signal, to transmit electromagnetic flux into an object under test, and to sense and generate output signals from transient electromagnetic flux in the object;
    an analog-to-digital converter configured to digitize the output signals from the probe and to supply a digitized transient response signal; and
    a processor configured to convolve a plurality of segments of the digitized transient response signal obtained over respective time intervals $\{\Delta t, \Delta t2, \ldots \Delta tn\}$ with a plurality of orthogonal functions to generate a plurality of orthogonal components corresponding to respective ones of a plurality of frequencies $f=\{1/\Delta t, 1/\Delta t2, \ldots, 1/\Delta tn\}$ and to a respective depth $\Delta z$ in the object.

14. The inspection system of claim 13, further comprising a display, wherein the processor is further configured to generating a plurality of linear profiles using the orthogonal components, and wherein the display is configured to display a XY scatter plot of the linear profiles in the complex plane.

15. The inspection system of claim 13, wherein the orthogonal functions comprise a sine function and a cosine function.

16. The inspection system of claim 15, wherein the processor is configured to determine a phase shift for the transient response signal based on a difference between an initial time (To) and a zero position of the sine function and to adjust a two-dimensional plot using the phase shift ($\phi$).

17. The inspection system of claim 13, wherein the processor is configured to detect a presence or absence of defect in the object using the orthogonal components.

18. A method for inspecting an object, the method comprising:
    applying a pulsed excitation signal to the object;
    detecting a transient response signal to the pulsed excitation signal;
    selecting a segment of the transient response signal obtained over a time interval $\Delta t$;
    convolving the segment of the transient response signal with a sine function and a cosine function to generate a plurality of orthogonal components corresponding to a fundamental frequency $f=1/\Delta t$; and
    using the orthogonal components corresponding to the fundamental frequency $f=1/\Delta t$ to detect a presence or an absence of a defect in the object, wherein the orthogonal components are selected from the group consisting of a real component, an imaginary component, a phase, an amplitude and combinations thereof, the method further comprising selecting a plurality of segments of the transient response signal obtained over respective time intervals $\{\Delta t2, \ldots \Delta tn\}$, wherein the convolving step is repeated for the plurality of segments to generate a plurality of sets of orthogonal components corresponding to respective ones of a plurality of frequencies $f=\{1/\Delta t2, \ldots, 1/\Delta tn\}$, and wherein each of the sets of orthogonal components corresponds to a respective depth $\Delta z$ in the object.

19. The method of claim 18, further comprising:
generating a plurality of linear profiles using the orthogonal components; and graphing the linear profiles in a complex plane.

* * * * *

UNITED STATES PATENT AND TRADEMARK OFFICE
CERTIFICATE OF CORRECTION

PATENT NO. : 7,389,206 B2
APPLICATION NO. : 11/502199
DATED : June 17, 2008
INVENTOR(S) : Plotnikov Page 1 of 1

It is certified that error appears in the above-identified patent and that said Letters Patent is hereby corrected as shown below:

In Column 9, Line 9, in Claim 1, after "convolving" insert -- the segment of --.

In Column 10, Line 17, in Claim 12, after "time" insert -- T --.

In Column 10, Line 49, in Claim 16, delete "(To)" and insert -- ($T_0$) --, therefor.

Signed and Sealed this

Eighteenth Day of August, 2009

David J. Kappos
*Director of the United States Patent and Trademark Office*